United States Patent
Lange et al.

(10) Patent No.: US 6,303,562 B1
(45) Date of Patent: Oct. 16, 2001

(54) COMPOSITIONS COMPRISING 2-(2-HYDROXYPHENYL)BENZENESULFINATE AND ALKYL-SUBSTITUTED DERIVATIVES THEREOF

(75) Inventors: Elaine A. Lange, Bellaire; Qun Lin, Spring, both of TX (US)

(73) Assignee: Enchira Biotechnology Corporation, The Woodlands, TX (US)

(*) Notice: Subject to any disclaimer, the term of this patent is extended or adjusted under 35 U.S.C. 154(b) by 0 days.

(21) Appl. No.: 09/596,968

(22) Filed: Jun. 20, 2000

Related U.S. Application Data

(63) Continuation of application No. 09/232,192, filed on Jan. 14, 1999, now abandoned.

(51) Int. Cl.[7] .......................... C11D 1/22; C07C 309/30; C07C 313/04
(52) U.S. Cl. .......................... 510/495; 510/493; 562/74; 568/33
(58) Field of Search .................. 562/74; 568/33; 510/493, 495

(56) References Cited

U.S. PATENT DOCUMENTS

| | | | |
|---|---|---|---|
| 2,271,635 | 2/1942 | Flett et al. | 252/161 |
| 3,812,194 | 5/1974 | Starer et al. | 260/623 |
| 3,821,272 | 6/1974 | House et al. | 260/457 |
| 5,104,801 | 4/1992 | Kilbane, II | 435/282 |
| 5,132,219 | 7/1992 | Kilbane, II | 435/195 |
| 5,232,854 | 8/1993 | Montcello | 435/282 |
| 5,344,778 | 9/1994 | Kilbane, II | 435/262 |
| 5,356,801 | 10/1994 | Rambosek et al. | 435/195 |
| 5,356,813 | 10/1994 | Monticello | 435/282 |
| 5,358,869 | 10/1994 | Kilbane | 435/282 |
| 5,358,870 | 10/1994 | Monticello et al. | 435/282 |
| 5,387,523 | 2/1995 | Monticello | 435/282 |
| 5,472,875 | 12/1995 | Monticello | 435/282 |
| 5,607,857 | 3/1997 | Grossman et al. | 435/282 |
| 5,973,195 | * 10/1999 | Lange et al. | 562/59 |

OTHER PUBLICATIONS da Mata, M.L.E.N., et al., "Steric and Electronic Effects in the Synthesis of Biaryls and their Heterocyclic Congeners using Intramolecular Free Radical [1,5] ipso Substitution Reactions," *Tetrahedron Letters*, 38(1):137–140 (1997).

Gray, K.A., et al., "Molecular Mechanisms of Biocatalytic Desulfurization of Fossil Fuels," *Nature Biotech.*, 14:1705–1709 (1996).

Izumi, Y., et al., "Selective Desulfurization of Dibenzothiophene by *Rhodococcus erythropolis* D–1," *Appl. Env. Microbiol.*, 60(1):223–226 (1994).

Lee, M.K., et al., "Sulfur–Specific Microbial Desulfurization of Sterically Hindered Analogs of Dibenzothiophene," *Appl. Environ. Microbiol.*, 61(12):4362–4366 (1995).

MacPherson, T., et al., "Application of SPME/GC–MS to Characterize Metabolites in the Biodesulfurization of Organosulfur Model Compounds in Bitumen," *Environ. Sci. Technol.*, 31:421–426 (1998).

(List continued on next page.)

Primary Examiner—John Hardee
(74) Attorney, Agent, or Firm—Hamilton, Brook, Smith & Reynolds, P.C.

(57) ABSTRACT

The present invention relates to certain alkylated 2-(2-hydroxyphenyl) benzenesulfinic acid and 2-(2-hydroxyphenyl)benzenesulfonic acid compounds and compositions which consist essentially of 2-(2-hydroxyphenyl) benzenesulfinic acid, 2-(2-hydroxyphenyl)benzenesulfonic acid and/or substituted derivatives thereof. The compositions of the invention are useful as hydrotropes and are also of use as, or as starting materials for, surfactants, and as starting materials for the synthesis of other useful chemicals such as, polymers and resins, solvents, adhesives and biocides.

8 Claims, 1 Drawing Sheet

Effect of additives on cloud point of 1 wt% Neodol 23-6.5

OTHER PUBLICATIONS

Olson, E.S., et al., "Characterization of Intermediates in the Microbial Desulfurization of Dibenzothiophene," *Energy & Fuels,* 7:159–164 (1993).

Omori, T., et al., "Desulfurization of Dibenzothiophene by *Corynebacterium* sp. Strain SY1," *Appl Env. Microbiol.,* 58(3):911–915 (1992).

Schetty, G., "Zur Kenntnis der 2–Oxy–1, 1'–diaryl–2'–sulfonsaure–sultone," *Helvetica Chimica Acta.,* 31(1):24–30 (1949).

van Afferden, M., et al., "Biochemical Mechanisms for the Desulfurization of Coal–Relevant Organic Sulfur Compounds," *Fuel,* 72(12):1635–1643 (1993).

Organikum, 15., Auflage, 1977, pp. 372–379 and 395–399.

Ullmans Encyclopedia der technischen Chemie, 4. Auflage, Band 10, 1975, Seiten 450–464.

* cited by examiner

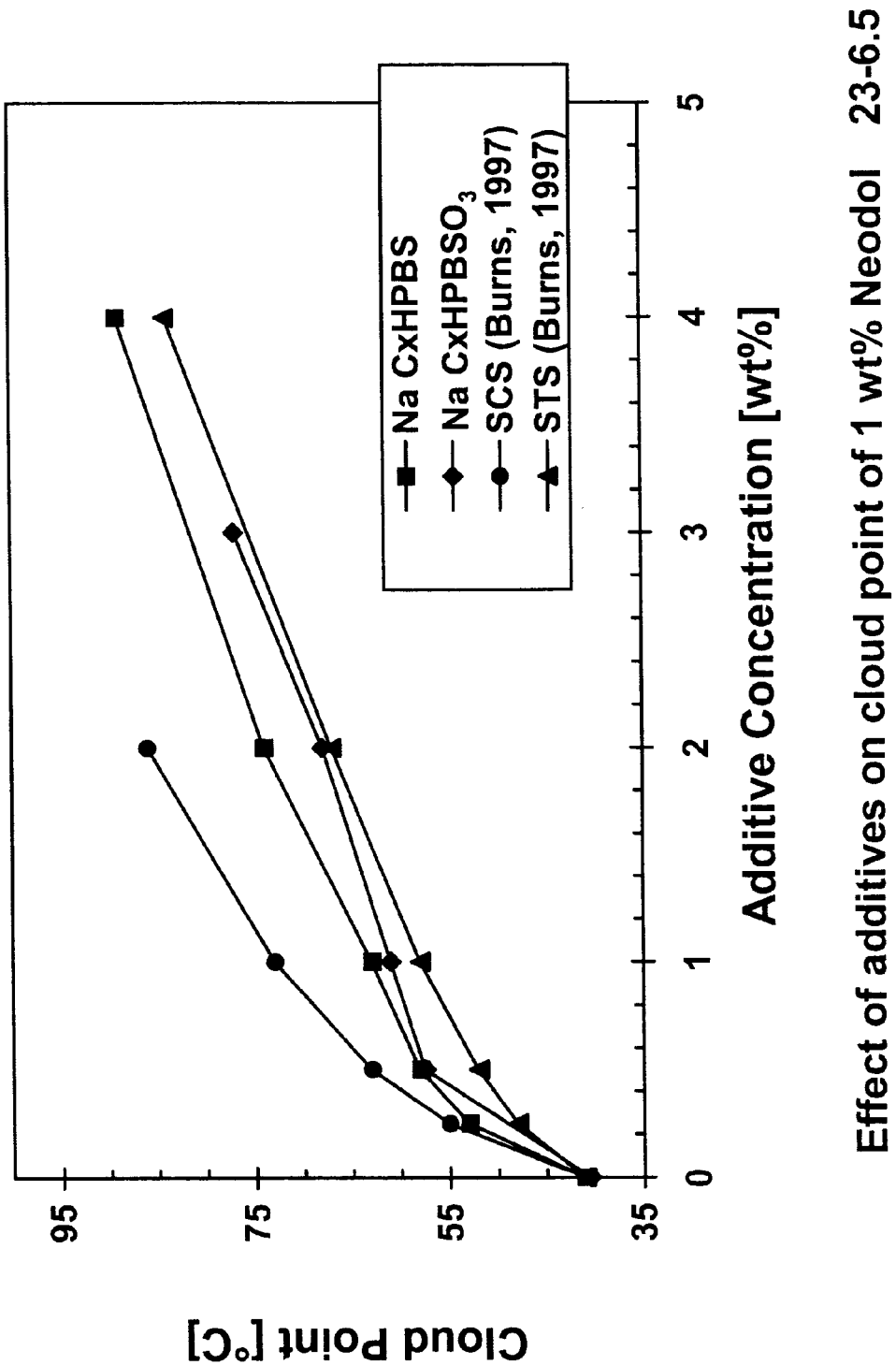
THE FIGURE

COMPOSITIONS COMPRISING 2-(2-HYDROXYPHENYL)BENZENESULFINATE AND ALKYL-SUBSTITUTED DERIVATIVES THEREOF

RELATED APPLICATIONS

This application is a continuation of U.S. patent application Ser. No. 09/232,192 filed Jan. 14, 1999 now abandoned, the entire teachings of which are incorporated herein by reference.

BACKGROUND OF THE INVENTION

Surfactants are amphiphilic compounds comprising a polar or ionic head group and a hydrophobic tail. Anionic surfactants have important commercial applications as wetting agents, detergents, oil additives and enhanced oil recovery agents. Anionic sulfonate surfactants are a commercially important class of detergents. Surfactants used in enhanced oil recovery processes also typically have sulfonate or sulfate polar head groups due to the aqueous solubility of such compounds in the presence of hard cations often present in such environments, such as $Mg^{2+}$ and $Ca^{2+}$. Such surfactants include alkylsulfonates, alkylarylsulfonates and petroleum sulfonates. More recently, the development of surfactant-based enhanced oil recovery methods has slowed dramatically, due, in part, to high surfactant costs. As a result, the development of low-cost surfactants derived from waste products, such as lignin, has been an active area of research in the petroleum industry.

Aromatic sulfonates, such as toluene sulfonate and cumene sulfonate, find application as hydrotropes, substances that increase the aqueous solubility of a material which otherwise has only limited aqueous solubility. Current research in the area of hydrotropes is focused on the development of materials having multifunctional properties.

Environmental concerns in regard to biodegradability and toxicity, as well as a desire for multifunctional compositions has driven research directed toward the development of new surfactants for detergents and other applications. There is, thus, a need for new, inexpensive starting materials for the preparation of surfactants, particularly surfactants which are suitable for use in an enhanced oil recovery process.

SUMMARY OF THE INVENTION

In one embodiment, the present invention relates to a composition which consists essentially of a 2-(2-hydroxyphenyl)benzenesulfinic acid or 2-(2-hydroxyphenyl) benzenesulfonic acid which is independently substituted at one or more ring positions by a substituted or unsubstituted linear, branched or cyclic $C_1$–$C_{24}$-alkyl, aryl or alkylaryl group. The substituted 2-(2-hydroxyphenyl)benzenesullinic acid or 2-(2-hydroxyphenyl) benzenesulfonic acid can also be present in the composition as a salt with one or more cations, as the corresponding sultine or sultone, or as a combination of two or more of the acid, salt and the sultine or sultone. The invention also includes a solution which consists essentially of a solvent and one of these substituted 2-(2-hydroxyphenyl) benzenesulfinic acid, 2-(2-hydroxyphenyl) benzenesulfonic acid, salts, sultines or sultones, or a combination thereof, dissolved therein.

In another embodiment, the invention relates to a 2-(2-hydroxyphenyl) benzenesulfinic acid or 2-(2-hydroxyphenyl)benzenesulfonic acid which is independently substituted at one or more ring positions by a linear, branched or cyclic, substituted or unsubstituted $C_6$–$C_{24}$-alkyl group and the remaining ring positions are independently unsubstituted or substituted by a linear or branched substituted or unsubstituted $C_1$–$C_5$-alkyl group. The compound can also exist as a salt with a cation or as the corresponding sultine or sultone.

In a further embodiment, the invention relates to compositions which consist essentially of two or more compounds selected from among 2-(2-hydroxyphenylbenzenesulfinic acid, substituted 2-(2-hydroxyphenyl)benzenesulfinic acids, 2-(2-hydroxyphenyl)benzenesulfonic acid and substituted 2-(2-hydroxyphenyl) benzenesulfonic acids, salts thereof, and sultines and sultones corresponding thereto. Suitable substituents can be present at one or more positions on either aromatic ring of the biphenyl nucleus, and include straight chain, branched or cyclic, substituted or unsubstituted $C_1$–$C_{24}$-alkyl groups, substituted and unsubstituted aryl groups, substituted and unsubstituted arylalkyl groups.

The present invention also provides a solution which consists essentially of a solvent and two or more compounds dissolved therein selected from among 2-(2-hydroxyphenylbenzenesulfinic acid, substituted 2-(2-hydroxyphenyl)benzenesulfinic acids, 2-(2-hydroxyphenyl) benzenesulfonic acids and substituted 2-(2-hydroxyphenyl) benzenesulfonic acids, salts thereof and sultines and sultones corresponding thereto, as described above.

In yet another embodiment, the invention relates to a method of alkylating substituted or unsubstituted 2-(2-hydroxyphenyl)benzenesulfinic acid or substituted or unsubstituted 2-(2-hydroxyphenyl)benzenesulfonic acid. The method comprises the step of reacting a substituted or unsubstituted 2-(2-hydroxyphenyl)benzenesulfinic acid or substituted or unsubstituted 2-(2-hydroxyphenyl) benzenesulfonic acid, with an alkene or substituted alkene under conditions suitable for alkylation of one or more ring positions of the 2-(2-hydroxyphenyl)benzenesulfinic acid or 2-(2-hydroxyphenyl) benzenesulfonic acid, thereby alkylating one or more ring positions of the 2-(2-hydroxyphenyl) benzenesulfinic acid or 2-(2-hydroxyphenyl) benzenesulfonic acid.

The present compositions can be used as hydrotropes and are also of use as, or as starting materials for, surfactants, and as starting materials for the synthesis of other useful chemicals such as, polymers and resins, solvents, adhesives and biocides.

BRIEF DESCRIPTION OF THE DRAWING

The figure is a graph comparing the effect of added CxHPBS, CxHPBSO3, sodium toluene sulfonate and sodium cumene sulfonate on the cloud point of NEODOL®23-6.5 surfactant.

DETAILED DESCRIPTION OF THE INVENTION

The present invention provides compositions which consist essentially of a compound of Formula I,

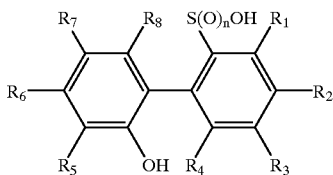

(I)

wherein n is 1 or 2, one or more of $R_1$–$R_8$ are each, independently, a substituted or unsubstituted linear, branched or cyclic $C_1$–$C_{24}$-alkyl, aryl or alkylaryl group and the remainder are each, independently, a hydrogen atom. In one embodiment, $R_1$–$R_8$ are each, independently, a hydrogen atom or a linear, branched or cyclic $C_1$–$C_6$-alkyl group. Preferably, one or two of $R_1$–$R_8$ is a linear, branched or cyclic $C_1$–$C_6$-alkyl group and the remainder are each a hydrogen atom. The compound of Formula I can also be present in the composition as a salt with one or more cations, the corresponding sultine or sultone, or as a combination of two or more of the acid, salt and sultine or sultone. In other embodiments, the compounds can be positional isomers of these compounds wherein the hydroxy and or sulfur moiety are independently positioned at the ortho, meta and para position at each ring.

The invention also includes a solution which consists essentially of a solvent, such as an aqueous solvent, an organic solvent or a mixture thereof, and one or more compounds of Formula I as described above, a salt thereof, the corresponding sultine or sultone or a combination thereof.

The term "aqueous solvent", as used herein, refers to water or water in which a buffer, inorganic salt, acid or base is dissolved, for example, to provide a desired pH or ionic strength. The organic solvent can be any organic solvent in which the compounds of Formula I are soluble, or an organic solvent which, when mixed with an aqueous solvent in suitable proportions, provides a medium in which the compound of Formula I, salt thereof, sultine or sultone is soluble. Preferably, the organic solvent is a polar solvent, for example, an alcohol, such as methanol or ethanol, dimethylsulfoxide, N,N-dimethylformamide, dichloromethane, chloroform, diethylether, acetonitrile, and tetrahydrofuran.

In another embodiment, the invention provides compounds of Formula I in which one or more of $R_1$–$R_8$ are each, independently, a substituted or unsubstituted linear, branched or cyclic $C_8$–$C_{24}$-alkyl group and the remainder are each, independently, a hydrogen atom or a substituted or unsubstituted linear, branched or cyclic $C_1$–$C_6$-alkyl, aryl or arylalkyl group, preferably a hydrogen atom or a linear or branched $C_1$–$C_6$-alkyl group. The invention further includes salts of these compounds with one or more cations and the corresponding sultines and sultones. In one embodiment, $R_7$ is a linear, branched or cyclic $C_8$–$C_{24}$-alkyl group. In another embodiment, $R_8$ or $R_{10}$ is a linear, branched or cyclic $C_8$–$C_{24}$-alkyl group. In yet another embodiment, two or more of $R_7$, $R_8$ and $R_{10}$ is a linear, branched or cyclic $C_8$–$C_{24}$-alkyl group.

In another embodiment, the present invention provides compositions which consist essentially of two or more compounds of Formula I in which $R_1$–$R_8$ are each, independently, hydrogen or a suitable substituent, such as a normal, branched or cyclic, substituted or unsubstituted $C_1$–$C_{24}$-alkyl group, a substituted or unsubstituted aryl group, a substituted or unsubstituted arylalkyl group, an amino group, a hydroxyl group, a cyano group, an acyl group, a nitro group, or a halogen atom, such as a fluorine, chlorine, bromine, or iodine atom.

Preferably, $R_1$–$R_8$ are each, independently, a hydrogen atom or a linear, branched or cyclic $C_1$–$C_{24}$-alkyl group. More preferably, $R_1$–$R_8$ are each, independently, a hydrogen atom or an unsubstituted linear or branched $C_1$–$C_6$-alkyl group, for example, a methyl group, an ethyl group or a linear or branched propyl, butyl, pentyl or hexyl group. In one embodiment, $R_1$–$R_8$ are selected from among methyl, ethyl and linear and branched propyl, butyl and pentyl, such that the total number of alkyl carbon atoms in each compound of Formula I is about five or less. In another embodiment, $R_1$–$R_8$ are selected from among methyl, ethyl and linear and branched propyl, butyl, pentyl and hexyl such that the total number of alkyl carbon atoms in each compound of Formula I is about 6 or less.

Suitable alkyl, aryl and arylalkyl substituents include halogen atoms, aryl groups, alkoxy groups, nitrile groups, acyl groups, amino groups and hydroxyl groups.

In one embodiment, the composition consists essentially of a compound of Formula I wherein each of $R_1$–$R_8$ is hydrogen, a salt thereof with a cation or the corresponding sultine or sultone or a combination thereof and one or more compounds of Formula I in which $R_1$–$R_8$ are each a hydrogen atom or a linear or branched $C_1$–$C_6$-alkyl group, a salt thereof, the corresponding sultine or sultone or a combination thereof. In another embodiment, the composition consists essentially of a compound of Formula I wherein each of $R_1$–$R_8$ is hydrogen, a salt thereof with a cation, the corresponding sultine or sultone or a combination thereof and one or more compounds of Formula I wherein one of $R_1$–$R_8$ is a methyl group and the remainder are each hydrogen, a salt thereof, the corresponding sultine or sultone or a combination thereof.

For example, the composition can include one or more compounds selected from among 2-(2-hydroxyphenyl) benzenesulfinic acid and 2-(2-hydroxyphenyl) benzenesulfonic acid; and one or more compounds selected from among methyl-substituted 2-(2-hydroxyphenyl) benzenesulfinic acid, methyl-substituted 2-(2-hydroxyphenyl)benzenesulfonic acid. Each of these compounds can be present in the composition as a salt with one or more cations, the corresponding sultine or sultone or a combination thereof. Suitable methyl-substituted compounds include 2-(2-hydroxy-3-methylphenyl) benzenesulfinic acid; 2-(2-hydroxy-4-methylphenyl)benzenesulfinic acid; 2-(2-hydroxy-5-methylphenyl)benzenesulfinic acid; 2-(2-hydroxy-6-methylphenyl) benzenesulfinic acid; 2-(2-hydroxyphenyl)-3-methylbenzenesulfinic acid; 2-(2-hydroxyphenyl)-4-methylbenzenesulfinic acid; 2-(2-hydroxyphenyl)-5-methylbenzenesulfinic acid; 2-(2-hydroxyphenyl)-6-methylbenzenesulfinic acid; 2-(2-hydroxy-3-methylphenyl) benzenesulfonic acid; 2-(2-hydroxy-4-methylphenyl) benzenesulfonic acid; 2-(2-hydroxy-5-methylphenyl)benzenesulfonic acid; 2-(2-hydroxy-6-methylphenyl)benzenesulfonic acid; 2-(2-hydroxyphenyl)-3-methylbenzenesulfonic acid; 2-(2-hydroxyphenyl)-4-methylbenzenesulfonic acid; 2-(2-hydroxyphenyl)-5-methylbenzenesulfonic acid; 2-(2-hydroxyphenyl)-6-methylbenzenesulfonic acid; salts thereof with a cation and the corresponding sultines and sultones.

The present invention also includes a solution which consists essentially of a solvent and two or more compounds of Formula I, as described above, each of which is dissolved in the solvent. The compounds of Formula I can each be present in the acid form, as a salt with a cation, as the corresponding sultine or sultone or as a combination thereof, as described above. The solvent can be an aqueous solvent, an organic solvent or a mixture thereof.

Compounds of Formula I can be present, partially or completely, in the deprotonated form, as a sulfinate or sulfonate salt with one or more suitable cations, for example, metal cations, such as alkali metal cations, alkaline earth metal cations or transition metal cations, or ammonium or primary, secondary, tertiary or quaternary ammonium ions. Preferably the cation is selected from among sodium ions, potassium ions, lithium ions, magnesium ions, calcium ions and ammonium ions.

Compounds of Formula I can also be present, partially or completely, in the form of the corresponding sultine or sultone. Suitable sultines and sultones are of Formula II, below, wherein m corresponds to n in Formula I and is 1 (sultine) or 2 (sultone). $R_1-R_8$ have the definitions given above for $R_1-R_8$ in Formula I. In a given compound of Formula 11, $R_1-R_8$ have the same identities as in the corresponding compound of Formula I.

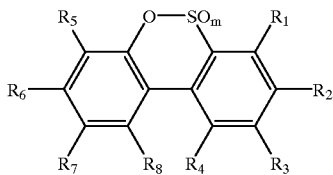

(II)

Preferably, 2-(2-hydroxyphenyl)benzenesulfinate and certain substituted derivatives thereof can be produced as intermediates in the biocatalytic desulfurization of a fossil fuel containing substituted or unsubstituted dibenzothiophenes. In another embodiment, the compositions of the invention can be made via a chemical or biological synthesis. Preferably, the disclosed compositions are advantageously derived from a petroleum biodesulfurization process. Suitable biodesulfurization processes and catalysts for use therein are described in U.S. Pat. Nos. 5,104,801; 5,358,869; 5,132,219; 5,344,778; 5,472,875; 5,232,854; 5,387,523; 5,356,813; 5,356,801 and 5,358,870, as well as U.S. patent application Ser. Nos. 08/351,754; 08/735,963; 08/851,088; 08/851,089 and 08/715,554. Each of the foregoing references is hereby incorporated by reference in its entirety.

The process of desulfurizing a fossil fuel disclosed in U.S. patent application Ser. No. 08/933,885, incorporated herein by reference in its entirety, offers several advantages in the production of the claimed compositions. This process employs a biocatalyst which catalyzes the conversion of dibenzothiophene to 2-(2-hydroxyphenyl) benzenesulfinate with little or no conversion of this product to 2-hydroxybiphenyl and sulfate.

Suitable biocatalysts for the oxidation of dibenzothiophene to 2-(2-hydroxyphenyl)benzenesulfinate include Rhodococcus sp. IGTS8, Corynebacterium sp. strain SY1, as disclosed by Omori et al., *Appl. Env. Microbiol.*, 58 : 911–915 (1992); *Rhodococcus erythropolis* D-1, as disclosed by Izumi et al., *Appl. Env. Microbiol.*, 60 :223–226 (1994); the Arthrobacter strain described by Lee et al., *Appl. Environ. Microbiol.* 61: 4362–4366 (1995) and the Rhodococcus strains (ATCC 55309 and ATCC 55310) disclosed by Grossman et al., U.S. Pat. No. 5,607,857, and Sphingomonas sp. strain AD 109, as described in U.S. patent application Ser. No.08/851,089, each of which is incorporated herein by reference in its entirety. Other suitable biocatalysts include recombinant organisms containing heterologous desulfurization genes, as disclosed, for example, in U.S. patent application Ser. No. 08/851,088, incorporated herein by reference.

Biodesulfurization is, generally, conducted by contacting the fossil fuel to be desulfurized with an aqueous phase comprising the biocatalyst. The water-soluble 2-(2-hydroxyphenyl) benzenesulfinate compounds can accumulate in the aqueous phase and can be separated from the fossil fuel with the aqueous phase. These compounds can then be isolated from the aqueous phase and purified using standard methods, such as chromatography, to produce the compositions of the invention.

Compounds of Formula I which include the sulfonic acid group (n=2) can prepared by oxidizing the corresponding sulfinic acid (n=1) obtained, for example, via a biodesulfurization process. The sulfinic acid group can be oxidized to the sulfonic acid group by reacting the sulfinic acid with a suitable oxidant, as is known in the art. Examples of suitable oxidants for this transformation include nitric acid, dioxygen, peroxides, such as hydrogen peroxide, m-chloroperbenzoic acid, peracetic acid and other peracids, hypochlorite, dimethyl sulfoxide, chromic acid, permanganate, dioxiranes, perborate and other oxidants which are well known in the art. Organic sulfinate compounds can also be oxidized to sulfonate compounds by $O_2$ in the presence of a suitable catalyst, such as $Fe^{3+}$. The sulfinic acid can be oxidized with one or more stoichiometric equivalents of the oxidizing agent to oxidize substantially all of the sulfinic acid to the sulfonic acid. The sulfinic acid can also be reacted with less than one stoichiometric equivalent of oxidizing agent to produce a mixture of sulfinic and sulfonic acids.

The invention also provides a method of alkylating a hydroxyphenylbenzenesulfinic acid compound or a hydroxyphenylbenzenesulfonic acid compound. The method comprises the step of reacting a hydroxyphenylbenzenesulfinic acid compound or hydroxyphenylbenzenesulfonic acid compound with a substituted or unsubstituted alkene under conditions suitable for alkylation of the hydroxyphenylbenzenesulfinic acid compound or hydroxyphenylbenzenesulfonic acid compound. This method can be used, for example, to prepare compounds of Formula I in which at least one of $R_1-R_8$ is a substituted or unsubstituted $C_{3-C24}$-alkyl group by alkylating a compound of Formula I in which at least one of $R_1-R_8$ is a hydrogen atom. A suitable alkylation method includes the step of contacting a first compound of Formula I wherein at least one of $R_1-R_8$ is a hydrogen atom with a substituted or unsubstituted alkene under suitable conditions for substitution of at least one hydrogen atom with an alkyl group, thereby producing a second compound of Formula I in which at least one hydrogen atom present in the first compound of Formula I is substituted by a $C_{3-C24}$-alkyl group. Typically, the reaction is conducted in solution at elevated temperature. In one embodiment, the reaction is conducted in a nonpolar solvent, such as a paraffin, for example, a liquid alkane, such as a $C_5-C_{18}$ alkane. In one embodiment, the reaction is conducted in dodecane at about 70° C. to about 100° C. Preferably, the compound of Formula I is reacted with at least about one molar equivalent of the alkene. More preferably, the compound of Formula I is reacted with at least about two molar equivalents of the alkene.

The alkene can be any alkene and is generally selected to provide an alkyl chain of a desired length. Suitable alkenes include terminal alkenes, such as a susbtituted or unsubstituted $C_{3-C_{24}}$-terminal alkene. Such alkenes include, but are not limited to, propane, 1-butene, 1-hexene, 1-octene, and 1-decene. The alkene can also be an internal alkene, for example, 2-butene, 2-hexene, 2-octene and 2-decene.

The compositions disclosed herein are useful starting materials for the synthesis of a variety of compositions. For example, U.S. patent application Ser. No. 09/044,272, incorporated herein by reference, discloses surfactant compounds derived from 2-(2-hydroxyphenyl)benzenesulfinate and 2-(2-hydroxyphenyl)benzenesulfonate. Compounds of Formula I in which at least one of $R_1$–$R_8$ is a $C_8$–$C_{24}$-alkyl group are also useful as surfactants without further transformation. Compositions including compounds of Formula I are also useful as starting materials for the synthesis of polymers, resins, adhesives, biocides and solvents.

The compositions of the invention are also useful as hydrotropes. In one embodiment, the present invention provides a composition in which one or more compounds of Formula I are present as hydrotropes. For example, the invention includes detergent compositions which comprise at least one compound of Formula I, as described above, or a salt thereof with a cation. In another embodiment, the detergent composition includes at least two compounds of Formula I, or one or more salts thereof with a suitable cation. The compound or compounds of Formula I can be present in the detergent composition in an amount from about 1% to about 20% by weight, preferably, from about 3% to about 5% by weight. The detergent composition of the invention further includes a detergent, for example, a phosphate detergent and others as are known in the art.

The invention will now be further described by the following examples.

EXAMPLES

Example 1

Analysis of 2-(2-hydroxyphenyl)benzenesulfinic Acid and Alkyl Substituted Derivatives from Biodesulfurization of Diesel Fuel Samples of two hydrotreated diesel fuels (Diesel 1 and Diesel 2) and a straight run diesel (Diesel 3) were desulfurized using a biodesulfurization process employing a Rhodococcus dszB-knockout strain as the biodesulfurization catalyst. Following the desulfurization process, the process water from each sample was analyzed by liquid chromatography/mass spectrometry. The distribution of 2-(2-hydroxyphenyl) benzenesulfinate ("HPBS") derivatives identified in the process water for each sample is presented in Table 1. These data indicate that each of these samples includes the parent HPBS as well as alkylated derivatives having from 1 to 4 additional carbon atoms, but that the relative amounts of each of these compounds vary from sample to sample. For example, for Diesels 2 and 3, the $C_2$-HPBS derivative (i.e., an HPBS derivative having 2 alkyl carbon atoms) was produced in greatest amount, while for Diesel 1, C3-HPBS (3 alkyl carbon atoms) was produced in greatest amount.

TABLE 1

| CxPPS | Diesel 1 | Diesel 2 | Diesel 3 |
| --- | --- | --- | --- |
| C0 | 1 | 9.18 | 1.55 |
| C1 | 9.09 | 33.84 | 19.31 |
| C2 | 28.26 | 44.69 | 37.1 |

TABLE 1-continued

| CxPPS | Diesel 1 | Diesel 2 | Diesel 3 |
| --- | --- | --- | --- |
| C3 | 57.72 | 11.3 | 30.3 |
| C4 | 3.91 | 1 | 8.75 |

Example 2

Recovery of 2-(2-hydroxyphenyl)benzenesulfinic Acid and Alkylated Derivatives from Biodesulfurization System As used in this and subsequent examples, "HPBS" and "HPBSO$_3$" refer to unsubstituted 2-(2-hydroxyphenyl) benzenesulfinic acid and 2-(2-hydroxyphenyl) benzenesulfonic acid, respectively. "CxHPBS" and "CxHPBSO$_3$" refer, respectively, to a mixture of 2 or more alkyl-substituted and/or unsubstituted 2-(2-hydroxyphenyl) benzenesulfinic acids and 2-(2-hydroxyphenyl)benzenesulfonic acids.

Biodesulfurization of diesel fuel was conducted in a pilot plant using the general process disclosed in U.S. patent application Ser. No. 08/933,885, and a recombinant Rhodococcus dszB knockout. Runs were completed in batch mode with the following typical conditions: 1:1 water-to-oil ratio; cell loading 10 g dry cell weight/L; water external emulsion; 12 to 14 hour run times. The CxHPBS was present in the process water. After each batch was finished, the oil-cell-water emulsion in the reactor was fed through an industrial centrifuge. The nozzle discharge from the centrifuge was fed to an Amicon cross-flow, hollow-fiber membrane filter, of which most passed through as filtrate and with some fluid wasted from the retentate side. Filtrate from the hollow-fiber membrane unit was fed to a tank, where the pH was adjusted to between pH 3 and 4. This fluid was then passed through an ion-exchange column. After the ion-exchange column was loaded, it was removed for regeneration using 1M sodium hydroxide. The column was then rinsed with distilled water and drained before being returned to service. The eight columns used in this project were loaded a total of 36 times. Before one run a methanol rinse was added before the sodium hydroxide in the regeneration procedure. The regenerate fractions were stored refrigerated until purification.

Isolation of CxHPBS from Ion Exchange Regenerate

The ion-exchange regenerate was acidified with HCl to pH 1, resulting in precipitation of the acid and formation of a gummy solid. The gummy solid was separated from the aqueous layer by centrifugation. The clear aqueous layer was then saturated with NaCl to precipitate more CxHPBS and then extracted with ethyl acetate. The gummy solid was also dissolved in ethyl acetate. Both ethyl acetate fractions were combined and the solvent was evaporated to give crude sultine as a thick brown liquid. After extraction, no CxHPBS was detectable in the aqueous phase by LC-MS analysis.

The crude sultine was loaded on a silica gel column. In a typical case, 150 g of crude sultine was loaded to a 1L capacity column. This column was eluted first with 9:1 hexane/ethyl acetate and then 8:2 hexane/ethyl acetate. The eluates were evaporated to yield a relatively pure sultine in the form of a thick yellowish liquid.

The purified sultine was transformed to CxHPBS by reacting with 1.1 equivalent of 50% NaOH. About 5 minutes after the addition of 50% NaOH, the mixture became hot and a significant amount of foam was formed. When the formation of foam ceased, 100 g deionized water was added for every 150 g of sultine. The resulting mixture was then heated in a 70° C. oil bath for 7 days and then freeze-dried to afford CxHPBS.

Another purification process explored for CxHPBS on a lab scale involved precipitation of CxHPBS from a refrigerated solution of the ion-exchange regenerate. The crystals formed under these conditions were determined to be a mixture of CxHPBS and sodium phosphate. The high level of phosphate was the result of earlier pH adjustment of the ion-exchange regenerate with phosphoric acid. In some cases concentration of the regenerate solution was required before crystallization and, on occasion, seed crystals were required. After isolation, the crystals were dissolved in a minimum amount of deionized water and the resulting solution was loaded onto a silica gel column. and eluted with 0.25% acetic acid. This process typically resulted in an isolated CxHPBS yield of about 29%.

Example 3

Comparison of CxHPBS Formation by Biodesulfurization Under Growth Conditions and Non-growth Conditions The production of CxHPBS by biodesulfurization ("BDS") in the presence and absence growth media was compared. In both experiments, the pH of the water was adjusted to approximately 3.5 before passing the liquid through the ion-exchange column.

The BDS process water with growth media had an organic carbon content of approximately 8,000 mg/L, of which 4,500 mg/L passed through the ion-exchange column. The feed water had a glucose concentration of 3,500 mg/L, indicating that the bulk of the organic carbon which is not adsorbed is residual glucose. The BDS process water without growth media had an organic carbon content of 4,000 mg/L, of which approximately 500 mg/L passed through the ion-exchange column. The adsorption capacity of the ion-exchange column was 7.4 g of organic carbon for BDS water growth media, and 18.5 g or organic carbon for BDS water without growth media. The diminished capacity with growth media is most likely caused by inorganic anions occupying exchange sites on the resin. LC/MS data indicated that CxHPBS was retained by the ion-exchange column, and concentrated in the sodium hydroxide regenerate for both experiments. The LC/MS data also showed that many compounds other than CxHPBS were present in the process water and ion-exchange regenerate for the experiment with BDS water with growth media. Purification of the CxHPBS was therefore required.

Example 4

Characterization of CxHPBS from Biodesulfurization System

Roughly 1 kg CxHPBS was purified by an extraction/chromatography procedure as described in Example 3. Portions of this material were retained as purified sultine (and as the sulfinic acid. Most of the sample was oxidized with hydrogen peroxide to produce the corresponding sulfonic acid ($CxHPBSO_3$).

The purity of the sultine, $CxHPBSO_3$ and CxHPBS samples was evaluated using a variety of analytical techniques. Assessment of the purity of the sulfonic acid sample using a variety of techniques indicated that the $CxHPBSO_3$ material was 97.5% pure, with the major impurities being sodium sulfate and sodium chloride. Organic contaminants were not present in detectable levels the final product.

One technique utilized was a 40 minute-HPLC method using a UV detector at 207 nm. This method can detect CxHPBS, $CxHPBSO_3$, the corresponding sultine and sultone, dibenzothiophene, dibenzothiophene sulfoxide, dibenzothiophene sulfone 2-hydroxybiphenyl, benzoic acid and salicylic acid. This analysis indicated that the CxHPBS and $CxHPBSO_3$ samples were quite pure. The UV trace of each peak between 5 to 14 minutes matches that of CxHPBS or $CxHPBSO_3$ standards. Small peaks eluting before 5 minutes and after 15 minutes were shown to be due to the solvent.

A 23 minute HPLC method for detection of glucose, acetate, succinate, ethanol and glycerol found none of these compounds present in the samples.

The $CxHPBSO_3$ sample were also analyzed using an HPLC method with UV detection at 280 nm instead and the ability to report a total ion count trace with m/z of 65 to 1000 can be reported. By this method, $CxHPBSO_3$ was found to be mainly composed of 2-(2-hydroxyphenyl) benzenesulfonic acid having from 0 to 4 alkyl carbon atoms with a trace amount of a compound or mixture of compounds having 5 alkyl carbon atoms.

Analysis for anions such as sulfate, chloride, phosphate and nitrate was performed using ion chromatography. Phosphate and nitrate were not found in these samples. Small amounts of chloride and sulfate were detected. If calculated as the sodium salt, these impurities were present as 2.5% sodium sulfate and 0.05% sodium chloride in the $CxHPBSO_3$ mixture. If sodium sulfate were present as a hydrate ($Na_2SO_4H_2O$), the salt would be 5.7% of the $CxHPBSO_3$ sample.

$^1$H-NMR and $^{13}$C-NMR Analysis of CxHPBS, $CxHPBSO_3$ and Sultine Samples

The $^1$H NMR spectrum of the sultine sample in $CDCl_3$ gave a very clear integration of aromatic protons and aliphatic protons. As shown in Table 2, the ratio of aromatic protons to aliphatic protons in the sultine sample is in the range of calculated ratios. The table also includes the ratios expected for sultines having a variety of alkyl substituents.

The CxHPBS and $CxHPBSO_3$ samples were partially dissolved ill acetone-$d_6$. In each case the acetone-insoluble residue was filtered off and dissolved in DMSO-$d_6$. The acetone-$d_6$ solutions had $^{13}$C NMR spectra consistent with the expected resonances with no indication of carbonyl or alkoxy groups. The $^{13}$C-NMR spectra of the DMSO-$d_6$ solutions indicated the presence of very small amounts of organic compounds.

TABLE 2

$^1$H NMR results for sultine sample and comparison with possible alkylated sultine derivatives

| | Ar—H | Aliphatic-H | Ratio of Ar—H to Aliphatic-H |
|---|---|---|---|
| sultine sample | 100 | 131.56 | 0.76 |
| $C_0$-sultine | 8 | 0 | |
| $C_1$-sultine | 7 | 3 (methyl) | 2.33 |
| $C_2$-sultine | 6 | 6 (dimethyl) | 1 |
| | 7 | 5 (ethyl) | 1.4 |
| $C_3$-sultine | 5 | 9 (trimethyl) | 0.56 |
| | 6 | 8 (methyl and ethyl) | 0.75 |
| | 7 | 7 (propyl or isopropyl) | 1 |
| $C_4$-sultine | 4 | 12 (tetramethyl) | 0.33 |
| | 5 | 11 (dimethyl and ethyl) | 0.45 |

TABLE 2-continued

¹H NMR results for sultine sample and comparison with possible alkylated sultine derivatives

| | Ar—H | Aliphatic-H | Ratio of Ar—H to Aliphatic-H |
|---|---|---|---|
| 6 | | 10 (diethyl, methyl and propyl, methyl and isopropyl) | 0.6 |
| 7 | | 9 (butyl, isobutyl, sec-butyl, tert-butyl) | 0.78 |

Analysis of the sultine sample by gas chromatography/mass spectrometry and all prominent fractions and resulting ions were attributable to the sultine. The sultine sample was also analyzed by gas chromatography/atomic emission detection with C, S, N, and O detectors. The N analysis trace indicated no nitrogen-containing compounds in the sample. C, S, and O analyses indicated that the prominent fractions (identified as sultine by GC-MS analysis) contain C, S, and O.

Example 5

Use of CxHPBS and CxHPBSO$_3$ as Hydrotropes

In the surfactants industry, hydrotropes are added in relatively high concentrations to liquid detergent formulations to increase the solubility of surfactants and to prevent crystal formation, thus also reducing viscosity. Examples of commercial hydrotropes include toluene sulfonates, xylene sulfonates, cumene sulfonates, naphthalene sulfonates, and benzoates. A benchmark property of a hydrotrope is its ability to increase the cloud point of a non-ionic surfactant at low levels. A mixture of alkylated 2-(2-hydroxyphenyl) benzenesulfinates, and the corresponding sulfonate compounds were evaluated as hydrotropes by measuring the elevation in cloud point of a 1wt% Shell Neodol®23-6.5 surfactant solution. The Neodol® surfactant was a non-ionic ethoxylated alcohol, prepared from a $C_{12}$–$C_{15}$ linear primary alcohol with an average of 3 moles ethylene oxide per mole alcohol. These test conditions were chosen to match those used in a recent published evaluation of several hydrotropes (Burns, R.L., "Hydrotropic Properties of Some Short Chain Alkylbenzene and Alkylnapthalene Sulfonates", presented at the American Oil Chemists Society Annual Meeting, May 11–14, 1997). The purified CxHPBS and CxHPBSO$_3$ material described above was used in these evaluations.

Results are shown in the Figure and indicate that the sulfinic acid salt and the sulfonic acid salt have hydrotropic properties intermediate between those reported by Burns for sodium toluene sulfonate (STS) and sodium cumene sulfonate (SCS).

Example 6

Alkylation of 2-(2-hydroxyphenyl)benzenesulfonic Acid 2-(2-Hydroxyphenyl)benzenesulfonic acid was prepared by passing the sodium salt through an Amberlyst 15 column. The 2-(2-hydroxyphenyl)benzenesulfonic acid was treated with alkene in dodecane as shown in Table 3 and the resulting products were analyzed by liquid chromatography/mass spectrometry. The results demonstrated that at 85–90° C., most of the 2-(2-hydroxyphenyl)benzenesulfonic acid treated with 1-decene was monoalkylated or either dialkylated or alkylated with dimerized alkene. Similar results were observed with CxHPBSO$_3$ produced as described in Example 2. Very high conversion was obtained in this reaction. When a similar reaction was carried out with 1-hexene, some trialkylation (or trimerization or dimerization of 1-hexene followed by alkylation) apparently occurred. In Table 3, the distributions of the starting material and products are represented as percentage of total area counts.

TABLE 3

Results of alkylation of HPBSO3 and CxHPBSO$_3$ with alpha-olefins

| Starting Material | Reaction Condition | Reaction Time (h) | Product(s) (%) | Unreacted Sulfonate (%) | Comments |
|---|---|---|---|---|---|
| HPBSO$_3$ 1-decene (2.8 equiv.) | Dodecane 85–90° C. | 17 | 29.76% $C_{10}$ and 69.72% $C_{20}$ | 0.52 | Products include: $C_{10}$ and $C_{20}$HPBSO$_3$ |
| | | 24 | 27.3% $C_{10}$ and 72.44% $C_{20}$ | 0.22 | |
| | | 31 | 85.79% $C_{10}$ and 14.21% $C_{20}$ | 0 | |
| HPBSO$_3$ 1-hexene (3.2 equiv.) | Dodecane 90–95° C. | 17 | 23.44% $C_6$, 73.14% $C_{12}$ and 2.72% $C_{18}$ | 0.7 | Products include: $C_6$, $C_{12}$ and $C_{18}$ HPBSO$_3$ |
| | | | 19.5% $C_6$, 76.9% $C_{12}$ and 3.3% $C_{18}$ | 0.3 | |
| CxHPBSO$_3$ 1-hexene (2.8 equiv.) | Dodecane 90–95° C. | 17 | 44.1% $C_{10}$ and 49.1% $C_{20}$ | 6.8 | Products include: $C_{10}$ and $C_{20}$ CxHPBSO$_3$ |
| | | | 41% $C_{10}$ and 55.4% $C_{20}$ | 3.6 $C_{0-4}$ | |

EQUIVALENTS

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims.

We claim:

1. A method of alkylating a (hydroxyphenyl)benzenesulfinic acid compound or a hydroxyphenylbenzenesulfonic acid compound comprising reacting the (hydroxyphenyl)benzenesulfinic acid compound or a hydroxyphenylbenzenesulfonic acid compound with an alkene or substituted alkene under conditions sufficient for alkylation of the (hydroxyphenyl)benzenesulfinic acid compound or a hydroxyphenylbenzenesulfonic acid compound, thereby producing an alkylated (hydroxyphenyl) benzenesulfinic acid compound or alkylated hydroxyphenylbenzenesulfonic acid compound.

2. The method of claim 1 wherein the (hydroxyphenyl) benzenesulfinic acid compound or a hydroxyphenylbenzenesulfonic acid compound is a first compound of Formula I,

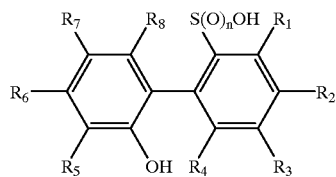

wherein at least one of $R_1$–$R_8$ is a hydrogen atom and the remainder are each, independently, a substituted or unsubstituted alkyl, aryl, or arylalkyl group, a halogen atom, an amino group or a cyano group, and the alkylated (hydroxyphenyl)benzenesulfonic acid compound or alkylated hydroxyphenylbenzenesulfonic acid compound is a second compound of Formula I, wherein $R_1$–$R_8$ in said second compound are identical to $R_1$–$R_8$ in said first compound, with the exception that at least one of $R_1$–$R_8$ which is a hydrogen atom in the first compound is a substituted or unsubstituted $C_1$–$C_{24}$-alkyl group in said second compound.

3. The method of claim 1 wherein in said first compound at least one of $R_7$ and $R_5$ in said first compound is a hydrogen atom and in said second compound at least one of $R_7$ and $R_5$ is a substituted or unsubstituted $C_3$–$C_{24}$-alkyl group.

4. The method of claim 2 wherein the alkene is a substituted or unsubstituted terminal alkene.

5. The method of claim 4 wherein the alkene is a terminal, linear or branched $C_3$–$C_{24}$-alkene.

6. The method of claim 1 wherein the reaction is conducted in an alkane solvent.

7. The method of claim 1 wherein the reaction is conducted at a temperature of about 70° C. to about 100° C.

8. A composition consisting essentially of:

one or more compounds of Formula I wherein n is 1 or 2 and $R_1$–$R_8$ are each hydrogen, or a salt thereof with a cation; and one or more compounds of Formula I wherein n is one or two, one of $R_1$–$R_8$ is methyl and the remainder are each hydrogen, or a salt thereof with a cation.

(I)

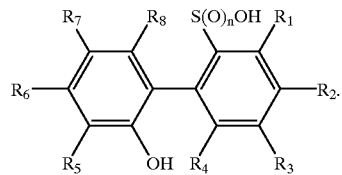

* * * * *

UNITED STATES PATENT AND TRADEMARK OFFICE
CERTIFICATE OF CORRECTION

PATENT NO. : 6,303,562 B1
DATED : October 16, 2001
INVENTOR(S) : Elaine A. Lange and Qun Lin It is certified that error appears in the above-identified patent and that said Letters Patent is hereby corrected as shown below:

Column 13,
Line 20, please delete "$C_1$-$C_{24}$-alkyl" and insert -- $C_3$-$C_{24}$-alkyl --.
Line 22, please delete "claim 1" and insert -- claim 2 --.

Column 14,
Line 4, please delete "claim 1" and insert -- claim 2 --.
Line 6, delete "claim 1" and insert -- claim 2 --.

Signed and Sealed this

Sixteenth Day of July, 2002

*Attest:*

JAMES E. ROGAN
*Attesting Officer*   *Director of the United States Patent and Trademark Office*